(12) United States Patent
Kobayashi et al.

(10) Patent No.: US 7,397,889 B2
(45) Date of Patent: Jul. 8, 2008

(54) IMAGING APPARATUS AND SUBJECT MOVING APPARATUS

(75) Inventors: Mitsuru Kobayashi, Tokyo (JP); Akira Izuhara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/408,706

(22) Filed: Apr. 21, 2006

(65) Prior Publication Data

US 2006/0239397 A1    Oct. 26, 2006

(30) Foreign Application Priority Data

Apr. 25, 2005    (JP) .............................. 2005-126152

(51) Int. Cl.
 *H05G 1/00* (2006.01)
(52) U.S. Cl. .............................. 378/20; 378/208; 5/601
(58) Field of Classification Search .................... 378/20, 378/208–209, 198; 5/600–601
See application file for complete search history.

(56) References Cited

U.S. PATENT DOCUMENTS

| 4,789,929 | A | * | 12/1988 | Nishimura et al. ............ 378/15 |
| 4,911,125 | A | * | 3/1990 | Sugawara et al. ........... 123/399 |
| 6,381,780 | B1 | | 5/2002 | Nose et al. |
| 7,024,710 | B2 | | 4/2006 | Izuhara |
| 2004/0141591 | A1 | | 7/2004 | Izuhara |
| 2005/0008116 | A1 | * | 1/2005 | Nishide et al. ................. 378/20 |
| 2006/0058639 | A1 | | 3/2006 | Izuhara et al. |

FOREIGN PATENT DOCUMENTS

JP    2004-173756    6/2004

* cited by examiner

*Primary Examiner*—Hoon Song
(74) *Attorney, Agent, or Firm*—Armstrong Teasdale LLP (57) ABSTRACT

It is intended to implement imaging in an efficient way. In a first period in which a cradle unit is driven under acceleration from a stationary state, the cradle unit is driven with a constant first torque value. In a second period which comes after the lapse of the first period and in which the cradle unit is driven under acceleration, the cradle unit is driven with a constant second torque value which is smaller than the first torque value.

15 Claims, 6 Drawing Sheets

IMAGING APPARATUS AND SUBJECT MOVING APPARATUS

CROSS REFERENCE TO RELATED APPLICATIONS

This application claims benefit of Japanese Application No. 2005-126152 filed Apr. 25, 2005.

BACKGROUND OF THE INVENTION

The present invention relates to an imaging apparatus and a subject moving apparatus.

An imaging apparatus, such as an X-ray CT (Computed Tomography) apparatus, acquires raw data by scanning a subject accommodated in an image pickup space and generates an image of the subject on the basis of the raw data.

In an X-ray CT apparatus, for instance, an X-ray tube and an X-ray detector are so arranged on a scanning gantry to place an image pickup space between them, and a subject moving apparatus moves a subject supported by a cradle unit into the image pickup space. And when helical scanning is to be performed for instance, the subject moving apparatus, after starting up the cradle unit by accelerating it at a prescribed rate of acceleration, slides it at a constant speed. It drives the cradle unit in this way, afterwards decelerates it at a prescribed rate of deceleration, and stops the unit. And when, for instance, the cradle unit is sliding at a constant speed in the image pickup space, the X-ray tube and the X-ray detector rotate around the subject supported by the cradle unit, and as X-rays are radiated in viewing directions around the subject, the X-ray detector acquires raw data in each viewing direction. And on the basis of the raw data in each viewing direction, sectional images of the subject in desired slicing positions and slicing thickness are generated by reconstruction (see JP-A No. 2004-173756).

Besides that, in the X-ray CT apparatus, the scanning gantry so moves the subject toward the cradle unit supporting it as to accommodate the subject in the image pickup space. And, in a similar way, X-rays are radiated in viewing directions around the subject, and the X-ray detector, acquiring raw data in each viewing direction, generates sectional images of the subject by reconstruction (see JP-A No. 2003-153889).

In driving the cradle unit or the scanning gantry as described above, a stepping motor is used for instance. In this case, the driving of the stepping motor is so controlled as to keep the absolute value of the torque constant irrespective of its number of revolutions.

In recent years, however, as the moving speed of the cradle unit or the scanning gantry is increased to realize a higher efficiency of imaging by increasing the scanning speed or the range of scanning, scanning may also be executed when its driving is accelerated or decelerated.

However, in such a case, such a trouble as desynchronization of the stepping motor which drives the cradle unit or the scanning gantry may occur, making it difficult to drive the cradle unit or the scanning gantry, and therefore required compatibility with the higher scanning speed or the expanded scanning range is sometime impossible to be achieved. For this reason, it is sometimes difficult according to the prior art to accomplish imaging efficiently. Especially when the cradle unit or the scanning gantry is to be driven under acceleration from an unmoving state, the aforementioned trouble could be more conspicuous.

SUMMARY OF THE INVENTION

Therefore, an object of the present invention is to provide an imaging apparatus and a subject moving apparatus apparatus which permit efficient execution of imaging.

In order to achieve the object stated above, an imaging apparatus according to the invention is an imaging apparatus for imaging a subject in an image pickup space, comprising: a cradle unit for supporting said subject; and a cradle driving unit for driving said cradle unit into said image pickup space, with a constant first torque value during a first period in which said cradle unit is driven under acceleration from a stationary state, and with a constant second torque value which is smaller than said first torque value during a second period which is after the lapse of said first period and in which said cradle unit is driven under acceleration.

In order to achieve the object stated above, a subject moving apparatus according to the invention is a subject moving apparatus for moving a subject, comprising: a cradle unit for supporting said subject, a cradle driving unit for driving said cradle unit, with a constant first torque value during a first period in which said cradle unit is driven under acceleration from a stationary state, and with a constant second torque value which is smaller than said first torque value during a second period which is after the lapse of said first period and in which said cradle unit is driven under acceleration.

In order to achieve the object stated above, an imaging apparatus according to the invention is an imaging apparatus for imaging a subject in an image pickup space, comprising: a scanning gantry unit for acquiring raw data on said subject in said image pickup space by scanning said subject; and a scanning gantry driving unit for driving said scanning gantry unit so as to accommodate said subject in said image pickup space, with a constant first torque value during a first period in which said scanning gantry unit is driven under acceleration from a stationary state, and with a constant second torque value which is smaller than said first torque value during a second period which is after the lapse of said first period and in which said scanning gantry unit is driven under acceleration.

According to the invention, it is possible to provide an imaging apparatus and a subject moving apparatus which permit efficient execution of imaging.

DETAILED DESCRIPTION OF THE INVENTION

One mode for embodiment of the present invention will be described below.

Embodiment 1

Embodiment 1 of the invention will be described below.

Figure 1:
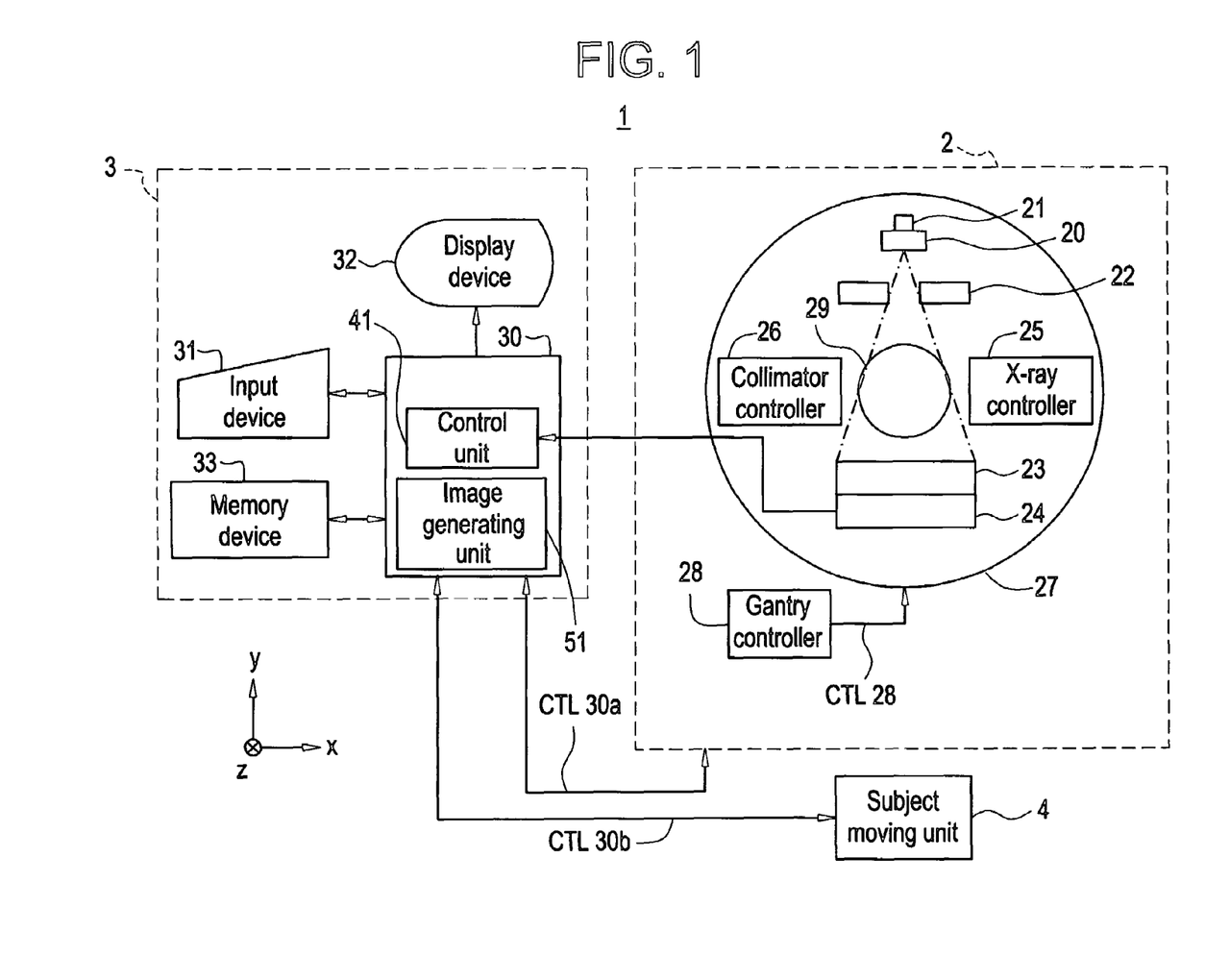
FIG. 1 is a configurational diagram showing the overall configuration of the X-ray CT apparatus 1 in Embodiment 1 of the present invention.
Figure 2:
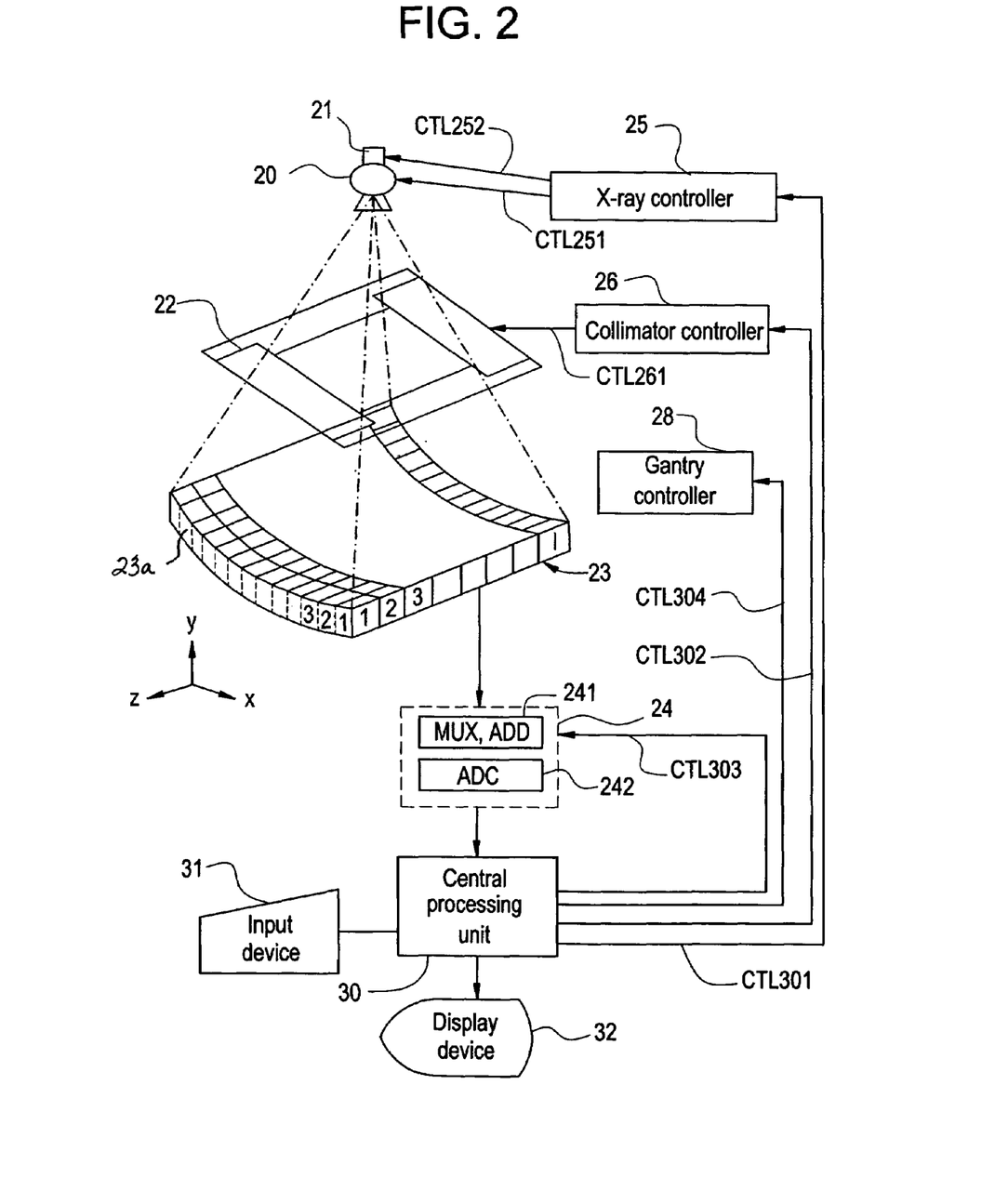
FIG. 2 is a configurational diagram showing essential parts of the X-ray CT apparatus 1 in Embodiment 1 of the invention.

FIG. 1 is a configurational diagram showing the overall configuration of an X-ray CT apparatus 1 in Embodiment 1 of the invention, and FIG. 2, a configurational diagram showing essential parts of the X-ray CT apparatus 1.

As shown in FIG. 1, the X-ray CT apparatus 1 has a scanning gantry 2, an operation console 3 and a subject moving unit 4. Each unit will be described in sequence.

The scanning gantry 2 has an X-ray tube 20, an X-ray tube moving unit 21, a collimator 22, an X-ray detector 23, a data collecting unit 24, an X-ray controller 25, a collimator controller 26, a rotary unit 27 and a gantry controller 28. The scanning gantry 2 scans a subject moved into an image pickup space 29 by the subject moving unit 4, and thereby obtains raw data of an image of the subject. In the scanning gantry 2 hereupon, the X-ray tube 20 and the X-ray detector 23 are opposite each other with the image pickup space 29, into which the subject is brought in, intervening between them.

The X-ray tube 20, which is of a rotating anode type for instance, radiates X-rays. The X-ray tube 20, as shown in FIG. 2, irradiates the target area of the subject with X-rays of a prescribed intensity via the collimator 22 on the basis of a control signal CTL 251 from the X-ray controller 25. Also, the X-ray tube 20 is turned around the subject in the columnar direction z, which is the body axis direction of the subject, by the rotary unit 27 to irradiate the subject with X-rays in viewing directions from around.

The X-ray tube moving unit 21, as shown in FIG. 2, moves the radiation center of the X-ray tube 20 in the columnar direction z, which is the body axis direction of the subject, within the image pickup space 29 in the scanning gantry 2 in accordance with a control signal CTL 252 from the X-ray controller 25.

The collimator 22, as shown in FIG. 2, is arranged between the X-ray tube 20 and the X-ray detector 23. The collimator 22 has, for instance, a plurality of shielding plates for shielding against X-rays, and the plurality of shielding plates are provided two each in the channel direction x and the columnar direction z. The collimator 22 causes the two shielding plates provided in each direction independent of each other in accordance with a control signal CTL 261 from the collimator controller 26, shapes the X-rays radiated from the X-ray tube 20 in a cone shape by intercepting them in each direction thereby to adjust the X-ray irradiated range.

The X-ray detector 23 detects via a cradle unit 101 of the subject moving unit 4 the X-rays radiated from the X-ray tube 20 and transmitted by the subject, and generates projection data from the subject as raw data. The X-ray detector 23, together with the X-ray tube 20, is turned around the subject by the rotary unit 27. And in the plurality of viewing directions around the subject, it detects X-rays transmitted by the subject and generates projection data.

As shown in FIG. 2, the X-ray detector 23 includes a plurality of detection elements 23a; the detection elements 23a are two-dimensionally arranged in an array form in, for instance, a channel direction i along the rotational direction in which the X-ray tube 20 is turned by the rotary unit 27 around the subject in the image pickup space 29 and the columnar direction j along the rotation axis, which constitutes the center axis of the rotation of the X-ray tube 20 by the rotary unit 27. For example in the X-ray detector 23, about 1,000 of the detection elements 23a are arrayed in the channel direction i and about 32 are arrayed in the columnar direction j. Further in the X-ray detector 23, a concavely curved cylindrical face is formed by the plurality of detection elements 23a which are two-dimensionally arranged.

The detection elements 23a constituting the X-ray detector 23 are composed, for instance, as solid detectors, and have scintillators (not shown) for converting X-rays into lights and photodiodes (not shown) for converting the lights converted by the scintillators into electric charges. Incidentally, the detection elements 23a are not limited to such ones, but may as well be semiconductor detection elements using cadmium telluride (CdTe) or the like, or ion chamber type detection elements using xenon (Xe) gas.

The data collecting unit 24 is provided for collection of X-ray data detected by the X-ray detector 23. The data collecting unit 24 collects X-ray projection data on the subject detected by each detection element 23a of the X-ray detector 23, and outputs them to the operation console 3. As shown in FIG. 2, the data collecting unit 24 has a selection/addition switch-over circuit (MUX, ADD) 241 and an analog-to-digital converter (ADC) 242. The selection/addition switch-over circuit 241 selects projection data from the detection elements 23a of the X-ray detector 23 or adds them in a different combination in accordance with a control signal CTL 303 from a central processing unit 30, and outputs the result to the analog-to-digital converter 242. The analog-to-digital converter 242 converts the projection data selected or added in a desired combination by the selection/addition switch-over circuit 241 from analog signals into digital signals, and outputs them to the central processing unit 30.

The X-ray controller 25, as shown in FIG. 2, outputs the control signal CTL 251 to the X-ray tube 20 in accordance with a control signal CTL 301 from the central processing unit 30 and controls the radiation of X-rays. The X-ray controller 25 controls, for instance, the tube current and radiation time of the X-ray tube 20. The X-ray controller 25 outputs the control signal CTL 252 to the X-ray tube moving unit 221 in accordance with the control signal CTL 301 from the central processing unit 30, and so performs control as to move the center of radiation of the X-ray tube 20 in the columnar direction z.

The collimator controller 26, as shown in FIG. 2, controls the collimator 22 by outputting the control signal CTL 261 to the collimator 22 in accordance with a control signal CTL 302 from the central processing unit 30, and shapes X-rays radiated from the X-ray tube 20.

The rotary unit 27, as shown in FIG. 1, is disk-shaped, having the image pickup space 29 formed in its central part. The rotary unit 27 drives, for instance, a motor (not shown) in accordance with a control signal CTL 28 from the gantry controller 28, and rotates around the body axis direction z of the subject in the image pickup space 29. The rotary unit 27 is mounted with the X-ray tube 20, the X-ray tube moving unit 21, the collimator 22, the X-ray detector 23, the data collecting unit 24, the X-ray controller 25 and the collimator controller 26. The rotary unit 27 supplies electric power to different units via a slip ring (not shown). And the rotary unit 27 causes those units to rationally move around the subject, and the positional relationships of the subject brought into the image pickup space 29 with those units to vary in relative terms in the rotational direction. The rotation of the rotary unit 27 enables the X-ray tube 20 to irradiate the subject with X-rays in each of the plurality of viewing directions from around the subject and the X-ray detector 23 to detect the X-rays transmitted by the subject in each viewing direction.

The gantry controller 28, as shown in FIG. 1 and FIG. 2, outputs the control signal CTL 28 to the rotary unit 27 in accordance with a control signal CTL 304 from the central processing unit 30 of the operation console 3, and so performs control as to cause the rotary unit 27 to rotate.

The operation console 3, as shown in FIG. 1, has the central processing unit 30, an input device 31, a display device 32 and a memory device 33.

The central processing unit 30 is composed of, for instance, of a computer and, as shown in FIG. 1, has a control unit 41 and an image generating unit 51.

The control unit 41 of the central processing unit 30 irradiates the subject with X-rays from the X-ray tube 20 in accordance with scanning conditions for scanning the subject, and performs scanning by so controlling different units as to detect X-rays transmitted by the subject with the X-ray detector 2. More specifically, the control unit 41 outputs a control signal CTL 30a to each unit in accordance with scanning conditions to have scanning executed. For instance, the control unit 41 outputs a control signal CTL 30b to the subject moving unit 4 to have the subject moving unit 4 move the subject between inside and outside the image pickup space 29. Also, the control unit 41 causes the rotary unit 27 of the scanning gantry 2 to rotate by outputting the control signal CTL 304 to the gantry controller 28. Further, the control unit 41 outputs the control signal CTL 301 to the X-ray controller 25 so as to have the X-ray tube 20 radiate X-rays. And the control unit 41 outputs the control signal CTL 302 to the collimator controller 26, and controls the collimator 22 to shape the X-rays. The control unit 42 also outputs the control signal CTL 303 to the data collecting unit 24, and so performs control as to collect projection data acquired by the detection elements 23a of the X-ray detector 23.

The image generating unit 51 of the central processing unit 30 reconstructs the sectional images of the subject on the basis of projection data acquired by the scanning gantry 2. The image generating unit 51, after subjecting projection data in a plurality of viewing directions of helical scanning to pre-treatments including sensitivity correction and beam hardening for instance, reconstructs them by the filtered back projection method to reconstruct and generate sectional images of the subject.

The input device 31 of the operation console 3 is composed of an input device, such as a keyboard or a mouse for instance. The input device 31 inputs to the central processing unit 30 various items of information including scanning conditions and information on the subject in accordance with inputting operation by the operator.

The display device 32 of the operation console 3 displays, on the basis of instructions from the central processing unit 30, the sectional images of the subject reconstructed by the image generating unit 51.

The memory device 33 of the operation console 3, consisting of a memory, stores various data including the sectional images of the subject reconstructed by the image generating unit 51 and programs. The data stored in the memory device 33 are accessed by the central processing unit 30 as required.

The subject moving unit 4 is provided to move the subject between inside and outside the image pickup space 29.

Figure 3:
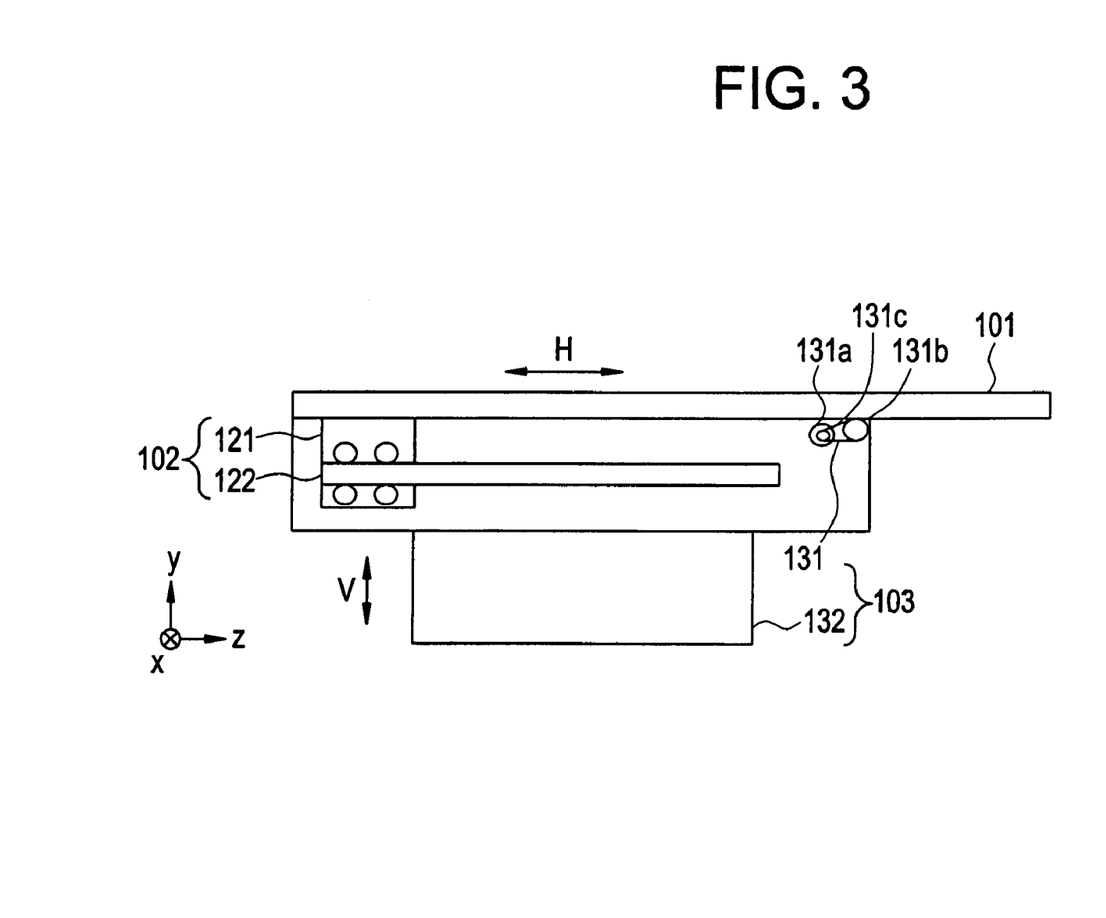
FIG. 3 is a profile showing the subject moving unit 4 in Embodiment 1 of the invention.

FIG. 3 is a profile showing the subject moving unit 4.

The subject moving unit 4, as shown in FIG. 3, has the cradle unit 101, a cradle supporting unit 102 and a cradle driving unit 103.

The cradle unit 101, provided with a mounting face on which the subject is to be mounted, supports the subject with that mounting face. The cradle unit 101, as shown in FIG. 3, is supported by the cradle supporting unit 102. The cradle unit 101 is movable by the cradle driving unit 103 in the horizontal direction H, substantially horizontal relative to the mounting face, and in the vertical direction V, substantially vertical to the mounting face, and moves between inside and outside the image pickup space 29 in the scanning gantry 2. More specifically, the cradle unit 101 is driven by the cradle driving unit 103 until it reaches a prescribed height in the vertical direction V and driven by the cradle driving unit 103 in the horizontal direction H to protrude out of the cradle supporting unit 102, and moves into the inside of the image pickup space 29.

The cradle supporting unit 102 so supports the cradle unit 101 as to cause the cradle unit 101 to slide in the horizontal direction H into the image pickup space 29. The cradle supporting unit 102, as shown in FIG. 3, has a carriage unit 121 and a guide rail unit 122.

The carriage unit 121, as shown in FIG. 3, is a truck which supports the cradle unit 101 and causes the cradle unit 101 to slide in the horizontal direction H to the image pickup space 29, and is supported by the guide rail unit 122. The carriage unit 121 is fixed in the cradle unit 101 toward the end in the farther position from the image pickup space 29. And the carriage unit 121, by sliding in the direction in which the guide rail unit 122 extends, slides the cradle unit 101 into the image pickup space 29.

The guide rail unit 122 is so formed as to extend in the direction in which the cradle unit 101 slides. The guide rail unit 122 supports the carriage unit 121 and makes slidable the cradle unit 101 fixed to the carriage unit 121.

The cradle driving unit 103, as shown in FIG. 3, has a horizontal driving unit 131 and a vertical driving unit 132, and drives the cradle unit 101 toward the image pickup space 29.

The horizontal driving unit 131 drives, in accordance with an instruction from the control unit 41, the cradle unit 101 to slide in the horizontal direction H. The horizontal driving unit 131 causes the cradle unit 101 to be accommodated in the image pickup space 29 by so moving it in the horizontal direction H as to protrude out of the cradle supporting unit 102. The horizontal driving unit 131 is equipped with a stepping motor 131a, a driving roller 131b which is turned by the stepping motor 131a to drive the cradle 101 in the horizontal direction H, and a driving belt 131c which transmits the revolutions of the stepping motor 131a to the driving roller 131b to have the driving roller 131b to roll. The horizontal driving unit 131 is enabled to slide the cradle unit 101 in the horizontal direction H as the stepping motor 131a rolls the driving roller 131b via the driving belt 131c and transmits the driving power to the cradle unit 101. Here, for instance, the horizontal driving unit 131 so moves the cradle unit 101 in the horizontal direction H as to shift to a constant speed after being accelerated at a prescribed rate of acceleration from a stationary state, and later stops the cradle unit 101 by decelerating it at a prescribed rate of deceleration.

The vertical driving unit 132 supports the cradle supporting unit 102 and, in accordance with an instruction from the control unit 41, drives in the vertical direction V the cradle unit 101 supported by the cradle supporting unit 102. The vertical driving unit 132 is equipped with, for instance, a parallel link type driving mechanism. The vertical driving unit 132, by driving the parallel link (not shown) with an actuator (not shown) for instance, moves the cradle unit 101 in the vertical direction V.

In the following paragraphs, the operations by which the cradle unit 101 mounted with the subject is driven by the cradle driving unit 103 to move the subject into the image pickup space 29 in the X-ray CT apparatus 1 in this embodiment will be described.

Figure 4A:
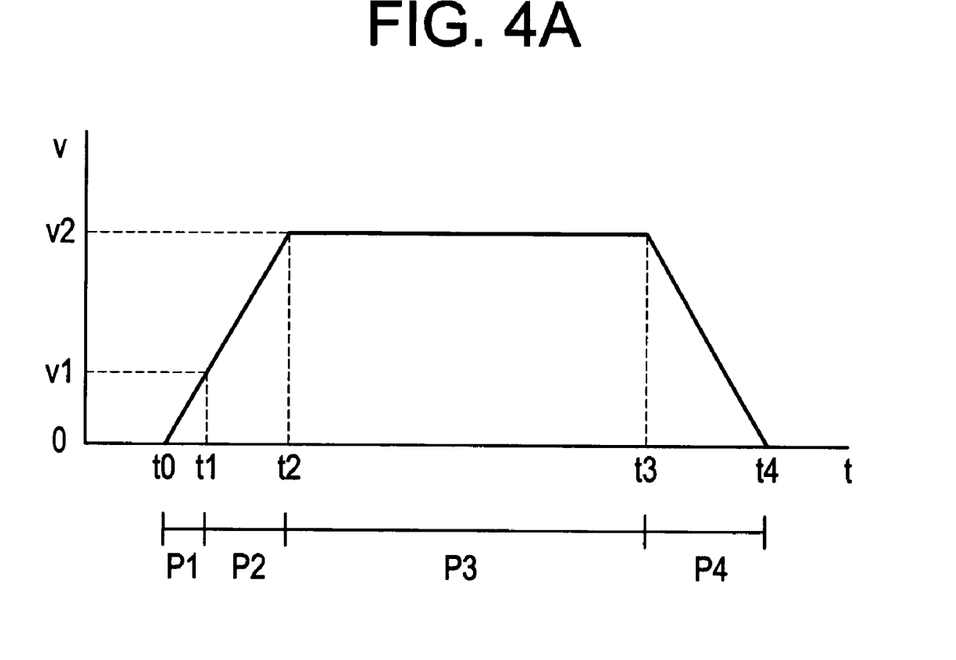
FIGS. 4a and 4b are diagrams showing the driving conditions of the cradle unit 101 and relationships to the torque value at the time the horizontal driving unit 131 of the cradle driving unit 103 drives the cradle unit 101 under those driving conditions in Embodiment 1 of the invention.
Figure 4B:
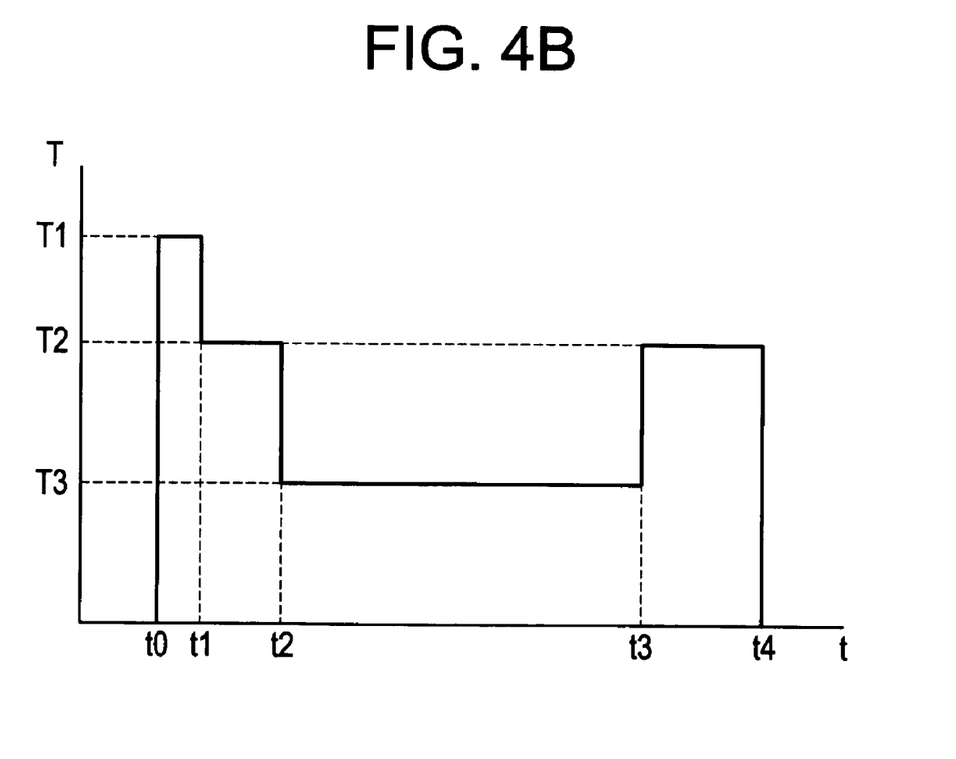

FIGS. 4 are diagrams showing the driving conditions of the cradle unit 101 and relationships to the torque value at the time the horizontal driving unit 131 of the cradle driving unit 103 drives the cradle unit 101 under those driving conditions. In FIGS. 4, FIG. 4(a) shows the driving conditions of the cradle unit 101, wherein the horizontal axis represents the time t and the vertical axis, the moving velocity v of the cradle unit 101. FIG. 4(b) shows the torque value T at the time the horizontal driving unit 131 of the cradle driving unit 103 drives the cradle unit 101 under the driving conditions shown in FIG. 4(a), wherein the horizontal axis represents the time t and the vertical axis, the torque value T.

In advance of moving the subject, which is a human body, into the image pickup space 29, the subject in a lying state is mounted on, and caused to be supported by, the mounting face of the cradle unit 101 positioned outside the image pickup space 29.

Next, the scanning conditions are set. In setting the scanning conditions, the operator inputs the various parameter conditions of the scanning conditions to the input device 31. For instance, as the scanning conditions, scanning parameters including the scanning system such as the helical scanning system, the frequency of scanning matching the number of images to be picked up, the tube amperage and the tube voltage of the X-ray tube 20, the duration of irradiation with X-rays, the slicing position and the scanning thickness are set.

Next, scanning of the subject is executed. In executing the scanning, the control unit 41 of the central processing unit 30 receives an instruction to start scanning is received from the operator via the input device 31, and the control unit 41 outputs the control signals CTL 30a and CTL 30b to the scanning gantry 2 and the subject moving unit 4 in accordance with the scanning conditions set as described above.

As a result of this, in the subject moving unit 4, the vertical driving unit 132 so moves the cradle unit 101 in the vertical direction H that the cradle unit 101 may match the height of the image pickup space 29 of the scanning gantry 2. After that, the horizontal driving unit 131 slides the cradle unit 101 in the horizontal direction H into the inside of the image pickup space 29 in accordance with the driving conditions of the cradle unit 101 shown in FIGS. 4.

First, as shown in FIG. 4(a), in a first period P1 during which the cradle unit 101 is driven under acceleration from a stationary state, as from a starting point t0 at which the moving of the cradle unit 101 is started after a first point of time t1, the horizontal driving unit 131 so drives the cradle unit 101 with a constant first torque value T1 as to achieve a constant rate of acceleration a as shown in FIG. 4(b). In other words, during the first period P1, the horizontal driving unit 131 drives the cradle unit 101 in the horizontal direction H with the constant first torque value T1 so that the velocity v increases at the constant rate of acceleration a from 0 (mm/s) to v1 (mm/s).

In this first period P1, the horizontal driving unit 131 drives the cradle unit 101 with the first torque value T1, which is a torque value calculated on the basis of the maximum frictional force fmax which arises when the cradle unit 101 is driven into the image pickup space 29.

It is known that the maximum frictional force fmax is increased by progression of the cradle unit 101 toward the image pickup space 29 with the protrusion of the cradle unit 101 out of the cradle supporting unit 102, and is varied by the deflection of the cradle unit 101. Therefore, an experiment is executed with varied factors such as the weight W of the subject mounted on the cradle unit 101, the distance z by which the cradle unit 101 has moved from its reference position and the deflection Δ of the cradle unit 101, and the static frictional force is derived from the results of the experiment as the maximum frictional force fmax. And by using the maximum frictional force fmax (N) derived from this experiment, the safety factor ϵ for the starting of the stepping motor 131a, the radius r (mm) of the driving roller 131b, the maximum load Wmax (kg), the maximum rate of acceleration a (mm/s$^2$), the reduction ratio from the stepping motor 131a to the driving roller 131b and the gear efficiency μ, the first torque value T1 (N·m) is calculated by the following Equation (1) and is set. Herein the first torque value T1 is calculated and set on the basis of the following assumption that, for instance, the safety factor ϵ for the starting of the stepping motor 131a is ϵ=1.6, the maximum load Wmax is Wmax=250 kg from the permissible maximum body weight of the subject, the weight of the cradle unit 101 and the weight of the carriage unit, the maximum rate of acceleration a is a=300 mm/s$^2$ and the gear efficiency μ is μ=0.9. More specifically, a torque value matching a driving force in excess of 200 N is set as this first torque value T1.

$$T1 = \epsilon \cdot r \cdot (W\max \cdot a + f\max)/\nu/\mu \qquad (1)$$

Further in this embodiment, the period from a stationary state of the cradle unit 101 until the generation of a frictional force capable of driving with a second torque value T2, to be described afterwards, which is smaller than the first torque value T1, is set as the first period P1, and the horizontal driving unit 131 drives the cradle unit 101 with the first torque value T1 in this set first period P1. Here the relationship between the duration of driving the cradle unit 101 with the first torque value T1 and the corresponding frictional force are figured out by experiment, and the period until the generation of a frictional force capable of driving with this second torque value T2 is set as the first period P1. In other words, the first period P1 is so set as to match the transient region of varying from a static frictional force to a dynamic frictional force. More specifically, for instance, the first period P1 is set to be a period shorter than 0.5 s during which the cradle unit 101 is driven over a distance not longer than 10 mm.

And as shown in FIG. 4(a), in a second period P2 which is a period of driving the cradle unit 101 with continuous acceleration after the lapse of the first period P1 until a second point of time t2 after the lapse of a prescribed length of time from the first point of time t1, the horizontal driving unit 131 drives the cradle unit 101 with the second torque value T2 which is constant and smaller than the first torque value T1 as shown in FIG. 4(b). In other words, during the second period P2, the horizontal driving unit 131 so drives the cradle unit 101 in the horizontal direction H that the velocity v may continuously increase from v1 (mm/s) to v2 (mm/s) at the constant rate of acceleration a by switching over stepwise during acceleration from the first torque value T1 to the second torque value T2 smaller than the first torque value T1. More specifically, during this second period P2, the cradle unit 101 is driven with a torque value matching a driving force of not greater than 200 N as the second torque value T2. It is driven with, for instance, the constant second torque value T2 of 1.2 N·m. To add, the cradle unit 101 is so driven here as to be accelerated similarly to the rate of acceleration during the first period P1.

And as shown in FIG. 4(a), in a third period P3 which is a period of driving the cradle unit 101 at a constant velocity v2 after the lapse of the second period P2 until a third point of time t3 after the lapse of a prescribed length of time from the second point of time t2, the horizontal driving unit 131 drives the cradle unit 101 with a third torque value T3 which is constant and smaller than the second torque value T2 as shown in FIG. 4(b). In other words, during the third period P3, the horizontal driving unit 131 so drives the cradle unit 101 in the horizontal direction H that the velocity v may become the constant velocity v2 (mm/s) by switching over stepwise from the second torque value T2 to the third torque value T3 smaller than the second torque value T2. It is driven with, for instance, the constant third torque value T3 of 0.7 N·m.

And as shown in FIG. 4(a), in a fourth period P4 which is a period of driving the cradle unit 101 under deceleration after the lapse of the third period P3 until a fourth point of time t4 after the lapse of a prescribed length of time from the third point of time t3, the horizontal driving unit 131 so drives the cradle unit 101 as to decelerate it with a fourth torque value T4 which is greater than the third torque value T3 and constant as shown in FIG. 4(b). In other words, during the fourth period P4, the horizontal driving unit 131 so drives the cradle unit 101 in the horizontal direction H that the velocity v may decrease from v2 (mm/s) to 0 (mm/s) at a constant rate of deceleration by switching over stepwise from the third torque value T3 to the second torque value T2 greater than the third torque value T3.

In this way, the subject moving unit 4 moves the subject mounted on the cradle unit 101.

And the X-ray controller 25 outputs the control signal CTL 252 to the X-ray tube 20, and causes the X-ray tube 20 to radiate X-rays. Then, the collimator controller 26 outputs the control signal CTL 302 to the collimator 22 to shape the X-rays from the X-ray tube 20. This causes the gantry controller 28 to output the control signal CTL 28 to the scanning gantry 2 and turn the rotary unit 27 of the scanning gantry 2. Further, the control unit 41 outputs the control signal CTL 303 to the data collecting unit 24, and controls so as to collect projection data acquired by the detection elements 23a of the X-ray detector 23 as raw data.

More specifically, when helical scanning is to be performed, while the cradle unit 101 mounted with the subject is being slid within the image pickup space 29 as described, the X-ray tube 20 irradiates that subject with X-rays in a plurality of viewing directions, the X-ray detector 23 detects the X-rays transmitted by the subject via the cradle unit 101 in each viewing direction to acquire raw data. After that, sectional images of the subject in desired slicing positions and slicing thicknesses are generated by the image generating unit 51 by reconstruction on the basis of raw data in each viewing direction. Here, after the image generating unit 51 subjects projection data in a plurality of viewing directions to pre-treatments including sensitivity correction and beam hardening, the data are reconstructed by the filtered back projection method to generate sectional images of the subject.

As described above, in the X-ray CT apparatus 1 in this embodiment, the horizontal driving unit 131 of the cradle driving unit 103 drives the cradle unit 101 with the constant first torque value T1 by using the stepping motor 131a in the first period P1 during which the cradle unit 101 is driven under acceleration from a stationary state. And in the second period P2 which is after the lapse of that first period P1 and in which the cradle unit 101 is driven under acceleration, the horizontal driving unit 131 drives the cradle unit 101 with the second torque value T2 which is smaller than the first torque value T1 and is constant by using the stepping motor 131a. Herein, the horizontal driving unit 131, during the first period P1, drives the cradle unit 101 with a torque value calculated on the basis of the maximum frictional force fmax which is generated when the cradle unit 101 is driven into the image pickup space 29 as the first torque value T1. Also, the horizontal driving unit 131 drives the cradle unit 101 with the first torque value T1 during the first period P1 in which the cradle unit 101 is driven from a stationary state until a sufficient frictional force for driving it with the second torque value T2 is generated. More specifically, the horizontal driving unit 131, during the first period P1, so drives the cradle unit 101 as not to let it move more than 10 mm with a torque value matching a driving force in excess of 200 N as the first torque value T1. And in the second period P2, it drives the cradle unit 101 with a torque value matching a driving force of not exceeding 200 N as the second torque value T2. As a result, such a trouble as desynchronization of the stepping motor 131a can be prevented in this embodiment, and driving of the cradle unit 101 at a higher rate of acceleration matching a higher scanning speed or an expanded scanning range can be achieved. Further in this embodiment, the safety requirements for the subject under the ICE standard can be satisfied. Therefore, this embodiment makes it possible to readily achieve efficient accomplishment of imaging and securing the safety of the subject at the same time.

Embodiment 2

Embodiment 2 of the present invention will be described below.

Figure 5:
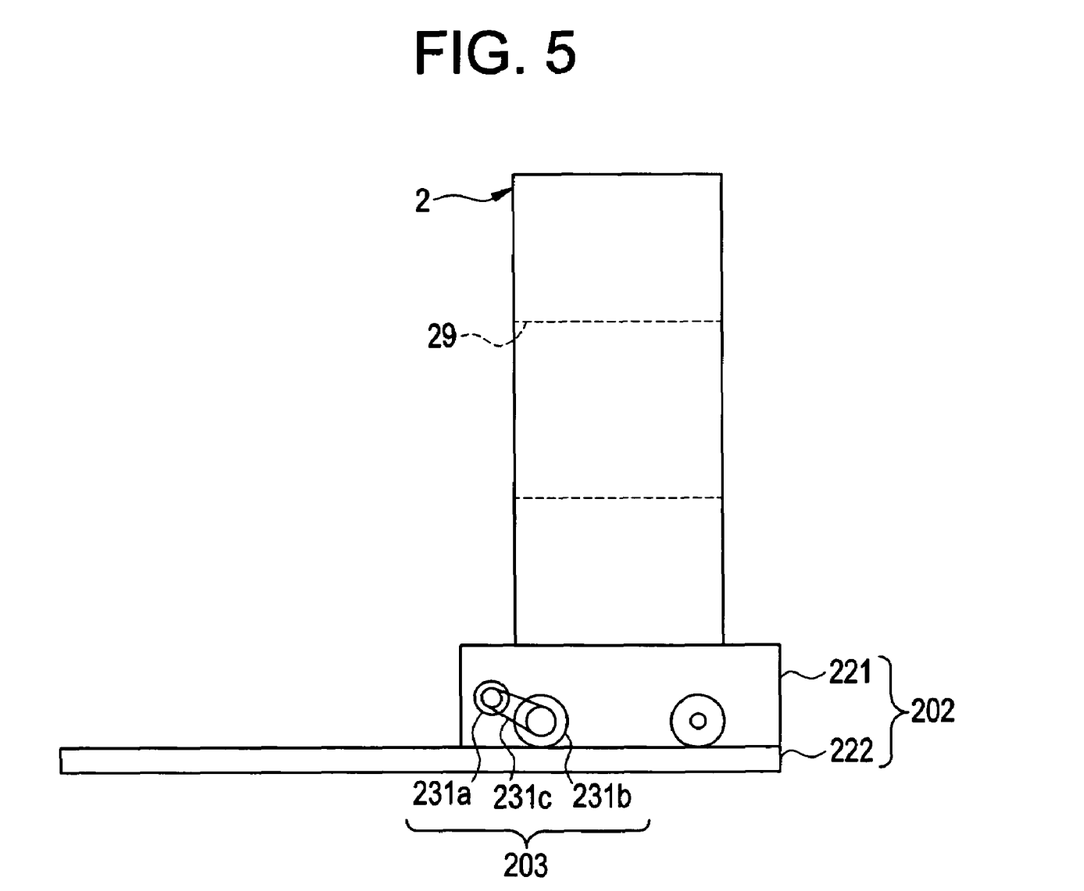
FIG. 5 is a profile showing the scanning gantry 2 in Embodiment 2 of the invention.

FIG. 5 is a profile showing the scanning gantry 2 of the X-ray CT apparatus 1 in this embodiment of the invention. The scanning gantry 2 in this embodiment, unlike in Embodiment 1, has a scanning gantry supporting unit 202 and a scanning gantry driving unit 203. Except in these respects, this embodiment is the same as Embodiment 1. Therefore, description of duplicated parts will be dispensed with.

The scanning gantry supporting unit 202 so supports the scanning gantry 2 that the scanning gantry 2 may slide in the horizontal direction H to accommodate the subject supported by the cradle unit 101 into the image pickup space 29. The scanning gantry supporting unit 202, as shown in FIG. 5, has a carriage unit 221 and a guide rail unit 222.

The carriage unit 221 of the scanning gantry supporting unit 202 which, as shown in FIG. 5, is a truck which supports the scanning gantry 2 and causes the scanning gantry 2 to slide in the horizontal direction H, is supported by the guide rail unit 222. The carriage unit 221 causes the scanning gantry 2 to slide by sliding in the extending direction of the guide rail unit 222, and thereby causes the subject mounted on the cradle unit 101 to be accommodated into the image pickup space 29 of the scanning gantry 2.

The guide rail unit 222 of the scanning gantry supporting unit 202 is so formed as to extend in the sliding direction of the scanning gantry 2. The guide rail unit 222 supports the carriage unit 221 and makes slidable the scanning gantry 2 fixed to the carriage unit 221.

The scanning gantry driving unit 203 so drives the scanning gantry 2 as to slide in the horizontal direction H in accordance with an instruction from the control unit 41 as shown in FIG. 5. The scanning gantry driving unit 203 is equipped with a stepping motor 231a, a driving roller 231b which is turned by the stepping motor 231a and drives the scanning gantry 2 in the horizontal direction H, and a driving belt 231c which transmits the revolutions of the stepping motor 231a to the driving roller 231b and thereby rolls the driving roller 231b. The scanning gantry driving unit 203 is enabled to slide the scanning gantry 2 in the horizontal direction H by the transmission of the driving force as the stepping motor 231a rolls the driving roller 231b via the driving belt 231c. Herein, for instance, the scanning gantry driving unit 203 so moves the scanning gantry 2 in the horizontal direction H for transition to a constant velocity after acceleration at a constant rate of acceleration from a stationary state, followed by deceleration at a constant rate of deceleration to stop the scanning gantry 2.

In the following paragraphs, the operations by which the scanning gantry 2 is driven by the scanning gantry driving unit 203 to move the subject into the image pickup space 29 in the X-ray CT apparatus 1 in this embodiment will be described.

Figure 6A:
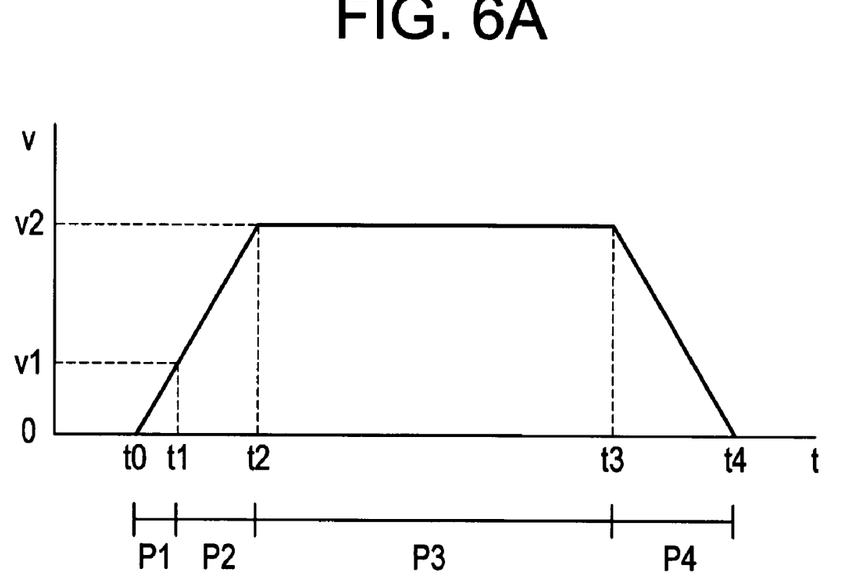
FIGS. 6a and 6b are diagrams showing the driving conditions of the scanning gantry 2 and relationships to the torque value at the time the scanning gantry driving unit 203 drives the scanning gantry 2 under those driving conditions in Embodiment 2 of the invention.
Figure 6B:
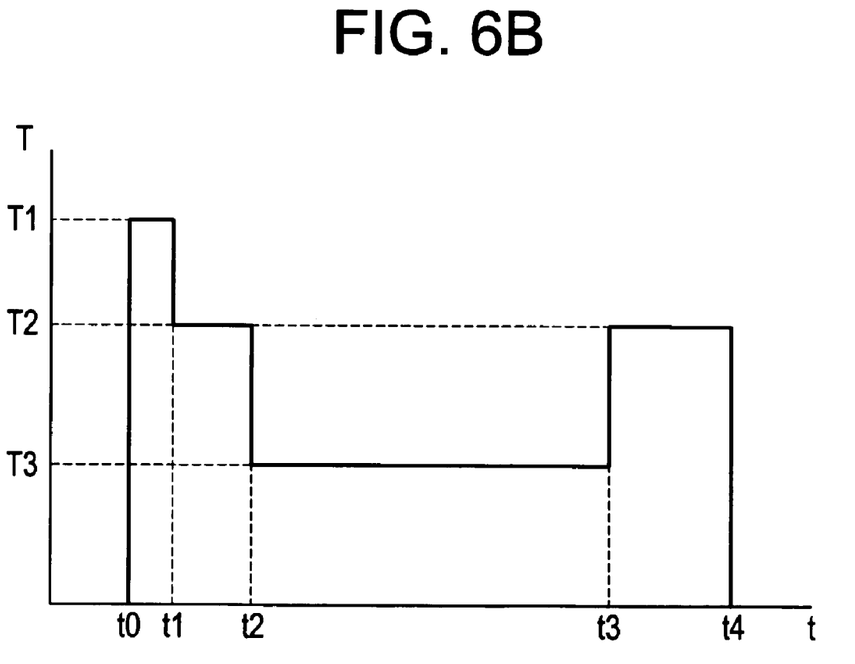

FIGS. 6 are diagrams showing the driving conditions of the scanning gantry 2 and relationships to the torque value at the time the scanning gantry driving unit 203 drives the scanning gantry 2 under those driving conditions. In FIGS. 6, FIG. 6(a) shows the driving conditions of the scanning gantry 2, wherein the horizontal axis represents the time t and the vertical axis, the moving velocity v of the cradle unit 101. FIG. 6(b) shows the torque value T at the time the scanning gantry driving unit 203 drives the scanning gantry 2 under the driving conditions shown in FIG. 6(a), wherein the horizontal axis represents the time t and the vertical axis, the torque value T.

Here, as shown in FIG. 6, similarly to the case of the cradle driving unit 103 in Embodiment 1 shown in FIGS. 4, the scanning gantry driving unit 203 drives the scanning gantry 2.

First, as shown in FIG. 6(a), in the first period P1 during which the scanning gantry 2 is driven under acceleration from a stationary state, as from a starting point t0 at which the moving of the scanning gantry 2 is started after a first point of time t1, the scanning gantry driving unit 203 so drives the scanning gantry 2 with a constant first torque value T1 as to achieve a constant rate of acceleration a as shown in FIG. 6(b). In other words, during the first period P1, the scanning gantry driving unit 203 drives the scanning gantry 2 in the horizontal direction H with the constant first torque value T1 so that the velocity v increases at the constant rate of acceleration a from 0 (mm/s) to v1 (mm/s).

In this first period P1, the scanning gantry driving unit 203 drives the scanning gantry 2 with the first torque value T1, which is a torque value calculated on the basis of the maximum frictional force fmax which arises when the scanning gantry 2 is driven. This maximum frictional force fmax is measured by experiment for instance, in the same way as in the case of the cradle unit 101 in Embodiment 1. After that, the first torque value T1 (N·m) is calculated by the foregoing Equation (1) and is set. More specifically, a torque value matching a driving force in excess of 200 N is set as this first torque value T1.

Further in this embodiment, the period from a stationary state of the scanning gantry 2 until the generation of a frictional force capable of driving with the second torque value T2, to be described afterwards, which is smaller than the first torque value T1, is set as the first period P1, and the scanning gantry driving unit 203 drives the scanning gantry 2 with the first torque value T1 in this set first period P1. Here the relationship between the duration of driving the scanning gantry 2 with the first torque value T1 and the corresponding frictional force are figured out by experiment, and the period until the generation of a frictional force capable of driving with this second torque value T2 is set as the first period P1.

And as shown in FIG. 6(a), in a second period P2 which is a period of driving the scanning gantry 2 with continuous acceleration after the lapse of the first period P1 until a second point of time t2 after the lapse of a prescribed length of time from the first point of time t1, the scanning gantry driving unit 203 drives the scanning gantry 2 with the second torque value T2 which is constant and smaller than the first torque value T1 as shown in FIG. 6(b). In other words, during the second period P2, the scanning gantry driving unit 203 so drives the scanning gantry 2 in the horizontal direction H that the velocity v may continuously increase from v1 (mm/s) to v2 (mm/s) at the constant rate of acceleration a by switching over stepwise during acceleration from the first torque value T1 to the second torque value T2 smaller than the first torque value T1. More specifically, during this second period P2, the scanning gantry 2 is driven with a torque value matching a driving force of not greater than 200 N as the second torque value T2.

And as shown in FIG. 6(a), in the third period P3 which is a period of driving the scanning gantry 2 at the constant velocity v2 after the lapse of the second period P2 until the third point of time t3 after the lapse of a prescribed length of time from the second point of time t2, the scanning gantry driving unit 203 drives the scanning gantry 2 with the third torque value T3 which is constant and smaller than the second torque value T2 as shown in FIG. 6(b). In other words, during the third period P3, the scanning gantry driving unit 203 so drives the scanning gantry 2 in the horizontal direction H that the velocity v may become the constant velocity v2 (mm/s) by switching over stepwise from the second torque value T2 to the third torque value T3 smaller than the second torque value T2.

And as shown in FIG. 6(a), in the third period P3 which is a period of driving the scanning gantry 2 at the constant velocity v2 after the lapse of the second period P2 until the third point of time t3 after the lapse of a prescribed length of time from the second point of time t2, the scanning gantry driving unit 203 drives the scanning gantry 2 with the third torque value T3 which is constant and smaller than the second torque value T2 as shown in FIG. 6(b). In other words, during the third period P3, the scanning gantry driving unit 203 so drives the scanning gantry 2 in the horizontal direction H that the velocity v may become the constant velocity v2 (mm/s) by switching over stepwise from the second torque value T2 to the third torque value T3 smaller than the second torque value T2.

As described above, in the X-ray CT apparatus 1 in this embodiment, the scanning gantry driving unit 203 drives the scanning gantry 2 with the constant first torque value T1 by using the stepping motor 231a in the first period P1 during which the scanning gantry 2 is driven under acceleration from a stationary state. And in the second period P2 which is after the lapse of that first period P1 and in which the cradle unit 101 is driven under acceleration, the scanning gantry driving unit 203 drives the scanning gantry 2 with the second torque value T2 which is smaller than the first torque value T1 and is constant by using the stepping motor 231a. Herein, the scanning gantry driving unit 203, during the first period P1, drives the scanning gantry 2 with a torque value calculated on the basis of the maximum frictional force fmax which is generated when the scanning gantry 2 is driven into the image pickup space 29 as the first torque value T1. Also, the scanning gantry driving unit 203 drives the scanning gantry 2 with the first torque value T1 during the first period P1 in which the scanning gantry 2 is driven from a stationary state until a sufficient frictional force for driving it with the second torque value T2 is generated. More specifically, the scanning gantry driving unit 203, during the first period P1, so drives the scanning gantry 2 as not to let it move more than 10 mm with a torque value matching a driving force in excess of 200 N as the first torque value T1. And in the second period P2, it drives the scanning gantry 2 with a torque value matching a driving force of not exceeding 200 N as the second torque value T2. As a result, such a trouble as desynchronization of the stepping motor 231a can be prevented in this embodiment, and driving of the scanning gantry 2 at a higher rate of acceleration matching a higher scanning speed or an expanded scanning range can be achieved. Further in this embodiment, the safety requirements for the subject under the ICE standard can be satisfied. Therefore, this embodiment makes it possible to readily achieve efficient accomplishment of imaging and securing the safety of the subject at the same time.

In the embodiment described above, the X-ray CT apparatus 1 corresponds to an imaging apparatus according to the invention. Also, the scanning gantry 2 in this embodiment corresponds to a scanning gantry unit according to the invention. Also, the subject moving unit 4 in this embodiment corresponds to a subject moving apparatus according to the invention. Also, the X-ray tube 20 in this embodiment corresponds to a radiant ray irradiating unit according to the invention. Also, the X-ray detector 23 in this embodiment corresponds to a radiant ray detecting unit according to the invention. Also, the cradle unit 101 in this embodiment corresponds to a cradle unit according to the invention. Also, the horizontal driving unit 131 in this embodiment corresponds to a cradle driving unit according to the invention. Also, the stepping motors 131a and 231a in this embodiment correspond to stepping motors according to the invention. Also, the scanning gantry driving unit 203 in this embodiment corresponds to a scanning gantry driving unit according to the invention.

Further, implementation of the present invention is not limited to the modes for implementation, but various modifications can be adopted.

For instance, though the foregoing description of embodiments referred to cases using X-rays as radiant rays for irradiation by the radiant ray irradiating unit, the choice is not limited to this. For instance, for instance, radiant rays such as gamma rays can be used as well.

The invention claimed is:

1. An imaging apparatus for imaging a subject in an image pickup space, comprising:
    a cradle unit for supporting said subject; and
    a cradle driving unit for driving said cradle unit into said image pickup space, with a constant first torque value during a first period in which said cradle unit is driven under acceleration from a stationary state, and with a constant second torque value which is smaller than said first torque value during a second period which is after the lapse of said first period and in which said cradle unit is driven under acceleration.

2. The imaging apparatus according to claim 1, wherein said cradle driving unit has a stepping motor for driving said cradle unit.

3. The imaging apparatus according to claim 1, wherein:
    said cradle driving unit drives said cradle unit during said first period with said first torque value calculated on the basis of the maximum frictional force which arises when said cradle unit is driven into said image pickup space.

4. The imaging apparatus according to claim 1 wherein:
    said cradle driving unit drives said cradle unit with said first torque value during said first period which is from a stationary state of said cradle unit until the generation of a frictional force capable of driving with said second torque value.

5. The imaging apparatus according to claim 1, wherein said cradle driving unit drives said cradle unit using a torque value corresponding to a driving force in excess of 200 N as said first torque value during said first period so as to move not more than 10 mm, and a torque value corresponding to a driving force of not greater than 200 N as said second torque value during said second period.

6. The imaging apparatus according to claim 1, further comprising:
    a scanning gantry unit which acquires raw data on said subject supported by said cradle unit by scanning said subject, comprising:
        a radiant ray irradiating unit which irradiates said subject being moved into said image pickup space with radiant rays; and
        a radiant ray detecting unit which obtains raw data by detecting said radiant rays radiated from said radiant ray irradiating unit and transmitted by said subject.

7. A subject moving apparatus for moving a subject, comprising:
    a cradle unit for supporting said subject; and
    a cradle driving unit for driving said cradle unit with a constant first torque value during a first period in which said cradle unit is driven under acceleration from a stationary state, and with a constant second torque value which is smaller than said first torque value during a second period which is after the lapse of said first period and in which said cradle unit is driven under acceleration, said first torque value calculated based on a maximum frictional force which arises when said cradle unit is driven into an image pickup space.

8. The subject moving apparatus according to claim 7, wherein said cradle driving unit has a stepping motor for driving said cradle unit.

9. The subject moving apparatus according to claims 7, wherein:
    said cradle driving unit drives said cradle unit with said first torque value during said first period which is from a stationary state of said cradle unit until the generation of a frictional force capable of driving with said second torque value.

10. A subject moving apparatus for moving a subject, comprising:
    a cradle unit for supporting the subject; and
    a cradle driving unit for driving said cradle unit with a constant first torque value during a first period in which said cradle unit is driven under acceleration from a stationary state, and with a constant second torque value which is smaller than said first torque value during a second period which is after the lapse of said first period and in which said cradle unit is driven under acceleration, said cradle driving unit drives said cradle unit using a torque value corresponding to a driving force in excess of 200 N as said first torque value during said first period so as to move not more than 10 mm, and a torque value corresponding to a driving force of not greater than 200 N as said second torque value during said second period.

11. An imaging apparatus for imaging a subject in an image pickup space, comprising:
    a scanning gantry unit for acquiring raw data on said subject in said image pickup space by scanning said subject; and
    a scanning gantry driving unit for driving said scanning gantry unit so as to accommodate said subject in said image pickup space, with a constant first torque value during a first period in which said scanning gantry unit is driven under acceleration from a stationary state, and with a constant second torque value which is smaller than said first torque value during a second period which is after the lapse of said first period and in which said scanning gantry unit is driven under acceleration.

12. The imaging apparatus according to claim 11, wherein:
    said scanning gantry driving unit has a stepping motor for driving said scanning gantry unit.

13. The imaging apparatus according to claim 11, wherein:
    said scanning gantry driving unit drives said scanning gantry unit during said first period with said first torque value calculated on the basis of the maximum frictional force which arises when said scanning gantry unit is driven into said image pickup space.

14. The imaging apparatus according to claims 11, wherein;
said scanning gantry driving unit drives said scanning gantry unit with said first torque value during said first period which is from a stationary state of said scanning gantry unit until the generation of a frictional force capable of driving with said second torque value.

15. The imaging apparatus according to claims 11, wherein:
said scanning gantry unit comprising:
a radiant ray irradiating unit which irradiates said subject in said image pickup space with radiant rays; and
a radiant ray detecting unit which obtains said raw data by detecting said radiant rays radiated from said radiant ray irradiating unit and transmitted by said subject.

\* \* \* \* \*